United States Patent
Wetzig et al.

(10) Patent No.: US 10,514,317 B2
(45) Date of Patent: Dec. 24, 2019

(54) GAS DENSITY INCREASE MEASUREMENT IN A FILM CHAMBER

(71) Applicant: INFICON GmbH, Cologne (DE)

(72) Inventors: Daniel Wetzig, Cologne (DE); Silvio Decker, Cologne (DE)

(73) Assignee: INFICON GmbH, Cologne (DE)

( * ) Notice: Subject to any disclaimer, the term of this patent is extended or adjusted under 35 U.S.C. 154(b) by 0 days.

(21) Appl. No.: 15/126,495

(22) PCT Filed: Mar. 12, 2015

(86) PCT No.: PCT/EP2015/055179
§ 371 (c)(1),
(2) Date: Sep. 15, 2016

(87) PCT Pub. No.: WO2015/140041
PCT Pub. Date: Sep. 24, 2015

(65) Prior Publication Data
US 2017/0108401 A1   Apr. 20, 2017

(30) Foreign Application Priority Data
Mar. 18, 2014  (DE) .................. 10 2014 205 032

(51) Int. Cl.
*G01M 3/32* (2006.01)
*G01N 21/3504* (2014.01)
(Continued)

(52) U.S. Cl.
CPC ........ *G01M 3/3218* (2013.01); *G01M 3/3209* (2013.01); *G01M 3/3281* (2013.01); *G01N 21/3504* (2013.01); *G01N 21/49* (2013.01); *G01N 21/64* (2013.01); *G01N 21/65* (2013.01); *G01N 2021/0364* (2013.01); *G01N 2021/6482* (2013.01); *G01N 2021/651* (2013.01)

(58) Field of Classification Search
CPC .... G01M 3/00; G01M 3/3218; G01M 3/3281; G01N 21/3504; G01N 21/49; G01N 21/64; G01N 21/65
USPC ........................................... 73/40.7
See application file for complete search history.

(56) References Cited

U.S. PATENT DOCUMENTS

| 4,031,742 A | 6/1977 | Michael et al. |
| 5,386,717 A * | 2/1995 | Toda ............... G01M 3/202 348/E5.105 |

(Continued)

FOREIGN PATENT DOCUMENTS

| DE | 19642099 A1 | 4/1998 |
| DE | 102005027023 A1 | 12/2006 |

(Continued)

OTHER PUBLICATIONS

INFICON, Product brochure Protec P3000 (XL) Helium Sniffer Leak Detector, pp. 1-6, 2010 (Year: 2010).*

*Primary Examiner* — David Z Huang
(74) *Attorney, Agent, or Firm* — The Webb Law Firm

(57) ABSTRACT

A method for a tightness test of a test piece (16) in a test chamber (10) whose wall is at least partly made of a flexible material, wherein said test piece is introduced into said test chamber and said test chamber is then evacuated, is characterized in that the tightness test is performed by measuring the gas density inside said test chamber (10) in the area outside said test piece (16).

6 Claims, 1 Drawing Sheet

(51) Int. Cl.
    *G01N 21/49*    (2006.01)
    *G01N 21/64*    (2006.01)
    *G01N 21/65*    (2006.01)
    *G01N 21/03*    (2006.01)

(56) References Cited

U.S. PATENT DOCUMENTS

| | | | | |
|---|---|---|---|---|
| 5,578,747 | A | * | 11/1996 | Nottingham .......... G01M 3/227 73/40 |
| 5,917,193 | A | | 6/1999 | Schroff et al. |
| 6,121,617 | A | * | 9/2000 | Hirayama .......... G01N 21/3504 250/343 |
| 2001/0016278 | A1 | * | 8/2001 | Onishi ................ H01M 6/5083 429/49 |
| 2004/0159144 | A1 | * | 8/2004 | Abelen ................ G01M 3/227 73/49.3 |
| 2013/0199274 | A1 | * | 8/2013 | Yamamoto ........... G01M 3/229 73/40.7 |
| 2017/0268957 | A1 | * | 9/2017 | Wetzig ................ G01M 3/3218 |

FOREIGN PATENT DOCUMENTS

| | | |
|---|---|---|
| DE | 102010048982 A1 | 3/2012 |
| DE | 102012200063 A1 | 7/2013 |
| EP | 0741288 A1 | 11/1996 |
| JP | 60111246 U | 7/1985 |
| JP | 6294740 A | 10/1994 |
| JP | 07129870 A | 5/1995 |
| JP | 10185752 A | 7/1998 |
| JP | 2006329650 A | 12/2006 |
| KR | 100781968 B1 | 11/2007 |
| WO | 0214824 A1 | 2/2002 |
| WO | 2013072173 A2 | 5/2013 |

\* cited by examiner

GAS DENSITY INCREASE MEASUREMENT IN A FILM CHAMBER

CROSS-REFERENCE TO RELATED APPLICATIONS

This application is the United States national phase of International Application No. PCT/EP2015/055179 filed Mar. 12, 2015, and claims priority to German Patent Application No. 10 2014 205 032.4 filed Mar. 18, 2014, the disclosures of which are hereby incorporated in their entirety by reference.

BACKGROUND OF THE INVENTION

Field of the Invention

The invention relates to a method for a tightness test of test pieces in test chambers having at least one flexible wall portion.

Description of Related Art

Such test chambers are evacuated after introduction of the test piece into the test chamber, whereby the flexible wall portion clings to the test piece to reduce the remaining residual volume in the test chamber in the area outside the test piece. The walls of the test chamber may completely be made of a flexible film, for example. Such test chambers are film chambers.

The test piece may be a packaging bag, for example a food package. The test piece is placed into the test chamber and the test chamber is then gastightly closed and evacuated. Here the term "evacuate" does not mean an absolute vacuum but rather a decrease of the pressure to such a pressure which is lower than the atmospheric pressure in the atmosphere surrounding the test chamber.

From DE 10 2005 027 023 it is known to measure the pressure inside the test chamber in the area outside the test piece after evacuation of the test chamber. This is based on the fact that gas exiting the test piece causes the pressure in the test chamber in the area outside the test piece to increase. For this purpose, the residual volume of the test chamber must be as small as possible, which is realized by the films clinging to the test piece.

The overall pressure increase inside the test chamber is temperature-dependent. On the one hand, a temperature change may be caused by the packaging material being heated as compared to the temperature in the test chamber such that exiting leakage gas causes a temperature increase. On the other hand, the pressure decrease in the test chamber causes the gas inside the test chamber to be cooled. Each temperature change of the gas inside the test chamber affects the test chamber pressure. It is not possible to simply differentiate between the temperature-related pressure change and the pressure change caused by exiting leakage gas.

SUMMARY OF THE INVENTION

It is an object of the invention to provide an improved method for a tightness test on test pieces in flexible test chambers.

Accordingly, for the purpose of a tightness test after introduction of the test piece into the test chamber and after evacuation of the test chamber, the density of the gas inside the test chamber in the area outside the test piece is measured. This can in particular be performed by measuring the time profile of the gas density. This gas density increases when gas exits the test piece due to a leakage and enters the test chamber volume. The density of a gas in a closed volume is independent of the temperature such that the tightness test method according to the invention can be performed independent of the temperature.

The result of the tightness test according to the invention is thus not affected and falsified by temperature variations. When the temperature of a gas increases, the energy of the gas and thus the velocity of the molecules and atoms increase, too. While the higher velocity leads to an increase of the pressure, the gas density, that is, the mass or the number of particle per volume unit, is temperature-independent and constant when the temperature increases.

The gas tightness measurement is performed with the aid of physical measuring methods which do not measure the "force per unit area" (gas pressure) but a collective particle characteristic which is proportional only to the number of particles in the volume (gas density) but has nothing to do with the temperature-dependent mean thermal velocity of the particles. For example, this may be performed by measuring the electric charge, the infrared absorption, the Rayleigh scattering, the Raman scattering, the fluorescence of the gas atoms/molecules or the gas heat conduction. The gas density measurement may also be performed with the aid of a gas-specific sensor (for example an oxygen sensor/ "lambda probe") or a sensor according to the Wise-Technology as offered by INFICON.

BRIEF DESCRIPTION OF THE DRAWINGS

Hereunder exemplary embodiments of the invention are described with reference to the figures in which.

DETAILED DESCRIPTION

Figure 1:
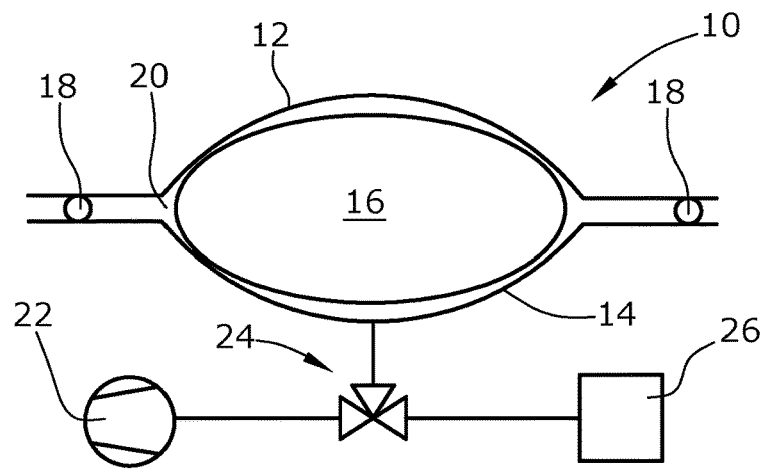
FIG. 1 shows a first exemplary embodiment.

In all exemplary embodiments, the test chamber 10 is a film chamber having an upper film layer 12 and a lower film layer 14. The two film layers 12, 14 are placed around the test piece 16 and placed on each other in the area outside the test piece 16. Between the film layers 12, 14 and in their boundary areas outside the test piece a sealing ring 18 is inserted for gastightly closing the test chamber 10. The sealing ring 18 serves only for illustrating the principle of gastightly sealing the film layers 12, 14 in their boundary areas. Instead of the sealing ring a double seal may be employed.

The test chamber volume 20 inside the test chamber 10 in the area outside the test piece 16 is reduced by evacuating the test chamber 10 until the film layers 12, 14 completely cling to the test piece 16. Evacuation, that is, the reduction of the pressure inside the test chamber 10, is performed by means of a vacuum pump 22 which is connected with the test chamber volume 20 via a valve assembly 24.

In each exemplary embodiment, the density of the gas is measured with the aid of an infrared absorption measuring cell 26 inside the test chamber volume 20, but other density measuring method are also conceivable.

In the first exemplary embodiment, the vacuum pump 22 and the measuring cell 26 are connected with the test chamber volume 20 via a three-way valve. Thus the gas line paths to the vacuum pump 22, to the measuring cell 26 and to the test chamber volume 20 can each be opened or shut off separately and independently of each other.

Figure 2:
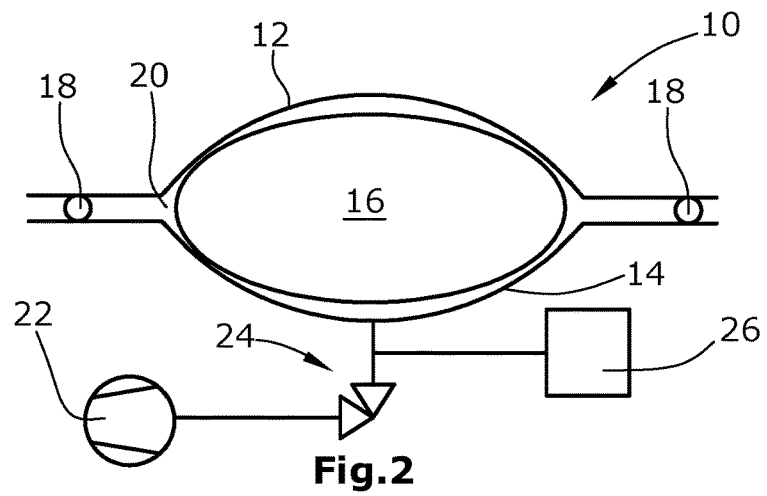
FIG. 2 shows a second exemplary embodiment.
Figure 3:
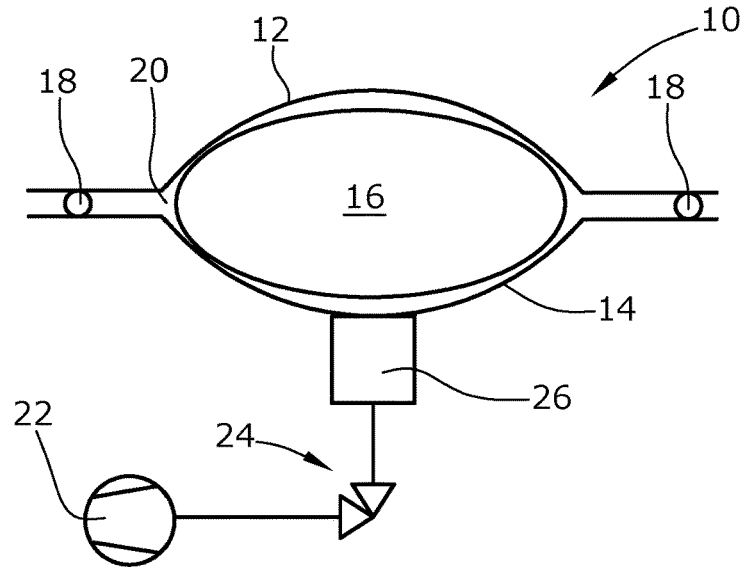
FIG. 3 shows a third exemplary embodiment.

In the exemplary embodiment of FIG. 2 the vacuum pump 22 is connected with the test chamber volume 20 via a two-way valve, wherein the measuring cell 26 is connected in a gas-conducting manner with the gas line path between the test chamber 10 and the valve assembly 24.

The third exemplary embodiment differs from the second exemplary embodiment in that the measuring cell 26 is contained in the gas line path from the test chamber 10 to the valve assembly 24.

The test piece 16, which may be a flexible food package, is first placed between the two film layers 12, 14 and then the film layers are sealed. With the aid of the vacuum pump 22 the test chamber 10 is then evacuated such that the test chamber volume 20 in the area outside the test piece 16 is minimal. Then the vacuum pump 22 is disconnected from the test chamber 10 with the aid of the valve assembly 24. Gas exiting the test piece 16, which flows into the test chamber 10, is fed to the infrared absorption measuring cell 26. In the measuring cell 26 the density of the gas is determined. The gas density is monitored during a predetermined period of time, wherein an increase of the gas density indicates a leakage in the test piece 16. The increase of the gas density over time is used for determining the magnitude of the leakage.

The invention claimed is:

1. A method for a tightness test of a test piece in a test chamber whose wall is at least partly made of a flexible material, comprising introducing said test piece into said test chamber, evacuating said test chamber such that the pressure within said test chamber is lower than the atmospheric pressure in the atmosphere surrounding said test chamber but greater than the pressure in an absolute vacuum, and measuring the gas density inside said test chamber in the area outside said test piece, wherein the tightness test is performed by measuring the collective density of all of the gas particles present within the test chamber in the area outside of the test piece.

2. The method for a tightness test according to claim 1, wherein the measurement of the gas density is performed by measurement of the electric charge, the infrared absorption, the Rayleigh scattering, the Raman scattering, the fluorescence, the gas heat conduction or with the aid of an oxygen sensor or a Wise-Technology sensor.

3. The method for a tightness test according to claim 1, wherein for the tightness test, no measurement of the gas pressure in the test chamber in the area outside the test piece is performed.

4. The method for a tightness test according to claim 1, wherein the gas from the test chamber is fed to a measuring cell in which the measuring of the gas density is performed.

5. The method for a tightness test according to claim 1, wherein the test chamber is a film chamber whose walls are made of flexible films.

6. The method for a tightness test according to claim 1, wherein the tightness test is performed by measuring the time profile of the gas density.

* * * * *